US00PP30006P2

(12) United States Plant Patent
van der Velde

(10) Patent No.: US PP30,006 P2
(45) Date of Patent: Dec. 18, 2018

(54) ***SEDUM* PLANT NAMED 'BNL-001'**

(50) Latin Name: *Sedum telephium*
Varietal Denomination: BNL-001

(71) Applicant: Henk van der Velde, Sliedrecht (NL)

(72) Inventor: Henk van der Velde, Sliedrecht (NL)

(73) Assignee: Burpee NL, B.V. (NL)

( * ) Notice: Subject to any disclaimer, the term of this patent is extended or adjusted under 35 U.S.C. 154(b) by 0 days.

(21) Appl. No.: 15/732,339

(22) Filed: Oct. 25, 2017

(51) Int. Cl.
*A01H 5/02* (2018.01)

(52) U.S. Cl.
USPC ..... Plt./479

(58) Field of Classification Search
USPC ..... Plt./479
See application file for complete search history.

*Primary Examiner* — Annette H Para
(74) *Attorney, Agent, or Firm* — Cassandra Bright

(57) ABSTRACT

A new and distinct *Sedum* x *Tacitus* cultivar named 'BNL-001' is disclosed, characterized large, dark purple to black foliage. Plants produce shoots from the side, forming an unique open-centered form. The new variety is a *Sedum*, plants are useful for a variety of ornamental purposes, including outdoor containers and landscape.

1 Drawing Sheet

Latin name of the genus and species: *Sedum telephium.*
Variety denomination: 'BNL-001'.

BACKGROUND OF THE INVENTION

The new *Sedum* cultivar is the product of a planned breeding program. The new variety originated from an open pollination of an unnamed proprietary, seed parent, *Sedum telephium* with a group of unpatented, unnamed *Sedum telephium*. The crossing was made during August of 2008 at a commercial greenhouse in Vista, Calif.

'BNL-001' was discovered by the inventor, in July of 2010 at a commercial greenhouse in Sommelsdijk, the Netherlands.

Asexual reproduction of the new cultivar 'BNL-001' was first performed in Boskoop, the Netherlands, at a commercial greenhouse by axial air sprouts, in October 2010. 'BNL-001' has since produced multiple generations and has shown that the unique features of this cultivar are stable and reproduced true to type.

SUMMARY OF THE INVENTION

The cultivar 'BNL-001' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BNL-001' These characteristics in combination distinguish 'BNL-001' as a new and distinct *Sedum* x *Tacitus* cultivar:

1. Deep purple to black foliage.
2. Plant form with an open center.
3. Unique large foliage.

PARENTAL COMPARISON

Plants of the new cultivar 'BNL-001' are similar to plants of the seed parent, in most horticultural characteristics, however, plants of the new cultivar 'BNL-001' differ in the following;

1. Foliage of the new variety is darker in purple/black coloration.
2. The new variety makes shoots from the sides of the plant, creating an open center in the plant habit not seen in the seed parent.
3. The new variety produces larger foliage than the seed parent.

COMMERCIAL COMPARISON

Plants of the new cultivar 'BNL-001' are comparable to the known, unpatented, *Sedum* 'Black Beauty'. Plants are similar in most horticultural characteristics; however, the new variety 'BNL-001' differs in the following:

1. Foliage of the new variety is darker in purple/black coloration.
2. The new variety makes shoots from the sides of the plant, creating an open center in the plant habit not seen in this comparator.
3. The new variety produces large foliage than the seed parent.

BRIEF DESCRIPTION OF THE PHOTOGRAPH

The accompanying photograph illustrates in full color typical plants of 'BNL-001' grown outdoors in Boskoop, NL. Age of the plant is approximately 2 years. The photographs were taken using conventional techniques and although colors may appear different from actual colors due to light reflectance it is as accurate as possible by conventional photographic techniques. No artificial light, photoperiodic treatments or chemical treatments were given to the plants.

DETAILED BOTANICAL DESCRIPTION

In the following description, color references are made to The Royal Horticultural Society Colour Chart, 2015 except where general terms of ordinary dictionary significance are used. The following observations and measurements describe 'BNL-001' plants grown outdoors in Boskoop, NL. Temperatures ranged from approximately 18° C. to 30° C. during the day and approximately 8° C. to 20° C. at night. No artificial light, photoperiodic treatments or chemical treatments were given to the plants. Measurements and numerical values represent averages of typical plant types. Botanical classification: *Sedum telephium* 'BNL-001'.

PROPAGATION

Type of propagation typically used: Axial air sprouts.
Time to initiate roots: About 14 days at approximately 22° C.
Root description: Fibrous, brown, not accurately measured with a color chart.

PLANT

Age of plant described: Approximately 2 years.
Container size of the plant described: In the ground.
Growth habit: Herbaceous perennial, semi-upright forming a flattened globular shape.
Height: Approximately 42.0 cm to top of highest leaf. Approximately 48.5 cm to top of highest inflorescence.
Plant spread: 81.3 cm.
Growth rate: Moderate.
Branching characteristics: Free branching, basal as well as lateral branches. Pinching is not required.
Length of primary lateral branches: Average 19 cm.
Diameter of lateral branches: 6 mm.
Quantity of primary lateral branches. About 26.
*Secondary branches per primary lateral branch.*—Average 4.
Characteristics of primary lateral branches:
*Form.*—Round.
*Color.*—Developing: Greyed-purple; 187A, covered with a thin waxy layer, colored greyed-purple; N187D. Mature: Greyed-purple; slightly lighter than N186C, fading lighter towards the base; N148D, covered with a thin waxy layer, colored greyed-purple; N187D. At Nodes: Yellow-green; 148A to 148B, covered with a thin waxy layer, colored greyed-purple; N187D. Near RHS Green 138B, flushed greyed-Purple N186C and N187B.
*Texture.*—Glabrous with very thing waxy layer colored near N187D.
*Strength.*—Very strong.
*Appearance.*—Matte.
*Aspect.*—Main stems in an average angle of 40° (varying between 80° and 0° (=vertical)), lateral stems in an average angle of 30° to main stem.
Internode: Average 4.4 cm.

FOLIAGE

Leaf:
*Arrangement.*—Opposite, single.
*Average length.*—Approximately 10.5 cm.
*Average width.*—Approximately 6.3 cm.
*Average depth.*—2 mm.
*Shape of blade.*—Ovate.
*Apex.*—Obtuse to broad bluntly acute.
*Base.*—Truncate.
*Margin.*—Coarsely blunt dentate.
*Texture of top surface.*—Glabrous.
*Texture of bottom surface.*—Glabrous.
*Appearance of top surface.*—Moderately glossy.
*Appearance of bottom surface.*—Matte.
Color:
*Young foliage upper side.*—Greyed-purple to black; in between N186A and 203B.
*Young foliage, under side.*—Yellow-green to greyed-green; in between 147A and 189A.
*Mature foliage, upper side.*—Greyed-purple to black; in between N186C and 203B, fading yellow-green at the base of the plant; 147A, covered with a thin waxy layer, colored greyed-purple; N187D and lighter.
*Mature foliage, under side.*—Yellow-green; 148A, tinged greyed-purple; N186C, covered with a thin waxy layer, colored greyed-purple.
*Venation.*—Type: Pinnate. Venation color upper side: RHS Greyed-purple; 187B and 187C. Venation color under side: RHS Greyed-orange 165A.
*Petiole.*—Sessile.

FLOWER

Natural flowering season: Spring, into Autumn.
Inflorescence type: Axillary and terminal compound cyme.
Inflorescence size (excluding peduncle):
*Height.*—Approximately 10.9 cm, including peduncle.
*Width.*—Approximately 5.6 cm.
Quantity of inflorescence per plant: 1000, depending upon maturity.
Quantity of flowers per inflorescence: Average 220.
Individual flowers:
*Length.*—Approximately 5 mm.
*Diameter.*—Approximately 1.0 cm.
*Longevity on plant.*—About 4 weeks.
*Persistent or self-cleaning.*—Persistent.
*Fragrance.*—None.
Petals:
*Arrangement.*—Rotate.
*Quantity per flower.*—5.
*Size.*—Length: Approximately 5 mm. Width: Approximately 2 mm.
*Margin.*—Entire.
*Shape.*—Ovate.
*Apex.*—Acute. *Petal color, under surface.*—Near Greyed-purple; 186A, veined white; 155A.
Petal color, fully opened:
*Upper surface.*—Near RHS Yellow-white; 158D, flushed red-purple; N74D.
*Under surface.*—Red-purple to Greyed-purple; in between 67B and 186A. Venation colored near White 155A.
*Color changes when aging.*—No significant change.
Bud:
*Shape.*—Near globular.
*Length.*—Approximately 4 mm.
*Diameter.*—Approximately 3.5 mm.
*Color.*—Near RHS Greyed-Purple 184B and 184C.
*Texture.*—Glabrous.
*Appearance.*—Glossy.
Calyx:
*Shape.*—Single whorl rotate, star-like.
*Length.*—1 mm.
*Base.*—Cuneate.
*Texture.*—Glabrous all surfaces.
*Appearance.*—Matte all surfaces.

*Petal color*.—When opening: Petal color, upper surface: Between White 155A and Red-Purple 69C.
*Diameter*.—3 mm.

Sepals:
*Arrangement*.—Rotate.
*Quantity*.—5.
*Shape*.—Narrow deltoid.
*Tip*.—Acute.
*Base*.—Broad cuneate.
*Margin*.—Entire.
*Texture*.—Glabrous all surfaces.
*Appearance*.—Matte all surfaces.
*Length of sepal*.—Approximately 1 mm.
*Width of sepal*.—Approximately 1 mm at widest point.
*Color upper surface*.—Near RHS Greyed-purple; 185A, striped and veined white; 155A, tip yellow-green; 147A.
*Color lower surface*.—Near RHS G Yellow-green; 147B.

Peduncle:
*Length*.—Average 8.8 cm
*Width*.—Approximately 3 mm.
*Strength*.—Moderately strong.
*Texture*.—Glabrous.
*Color*.—Near RHS Greyed-purple; 187A, covered with a thin waxy layer, colored greyed-purple; N187D and lighter.

Pedicels:
*Length*.—Approximately 4 mm.
*Width*.—Approximately 1 mm.
*Aspect*.—Straight.
*Strength*.—Moderately strong.
*Texture*.—Glabrous.
*Color*.—Near RHS Greyed-orange; 177A.

REPRODUCTIVE ORGANS

Stamens: (Androecium).
*Number*.—Average 10.
*Filament length*.—Approximately 3.5 mm.
*Filament color*.—Near RHS Greyed-purple; 186D.
*Anther length*.—0.75 mm.
*Anther color*.—Near RHS Greyed-red; 179B.
*Anther shape*.—Basifixed, broad ovate.
*Pollen color*.—Near RHS Yellow 4C.
*Pollen quantity*.—Moderate.

Pistil: (Gynoecium).
*Number*.—Average 5.
*Length*.—Approximately 0.5 mm.
*Style color*.—Near Greyed-purple; 187C.
*Style length*.—Approximately 0.3 cm.
*Stigma*.—Shape: Linear. Color: Near Greyed-purple; 187C. Ovary Color: Near RHS Red-purple; 59C.

OTHER CHARACTERISTICS

Fruits and seeds: Not observed to date.
Temperature tolerance: Tolerates temperatures from approximately −20° C. to at least 35° C.
Disease/pest resistance: Neither resistance nor susceptibility to normal diseases and pests of *Sedum* observed.

What is claimed is:

1. A new and distinct cultivar of *Sedum* x *Tacitus* plant named 'BNL-001' as herein illustrated and described.

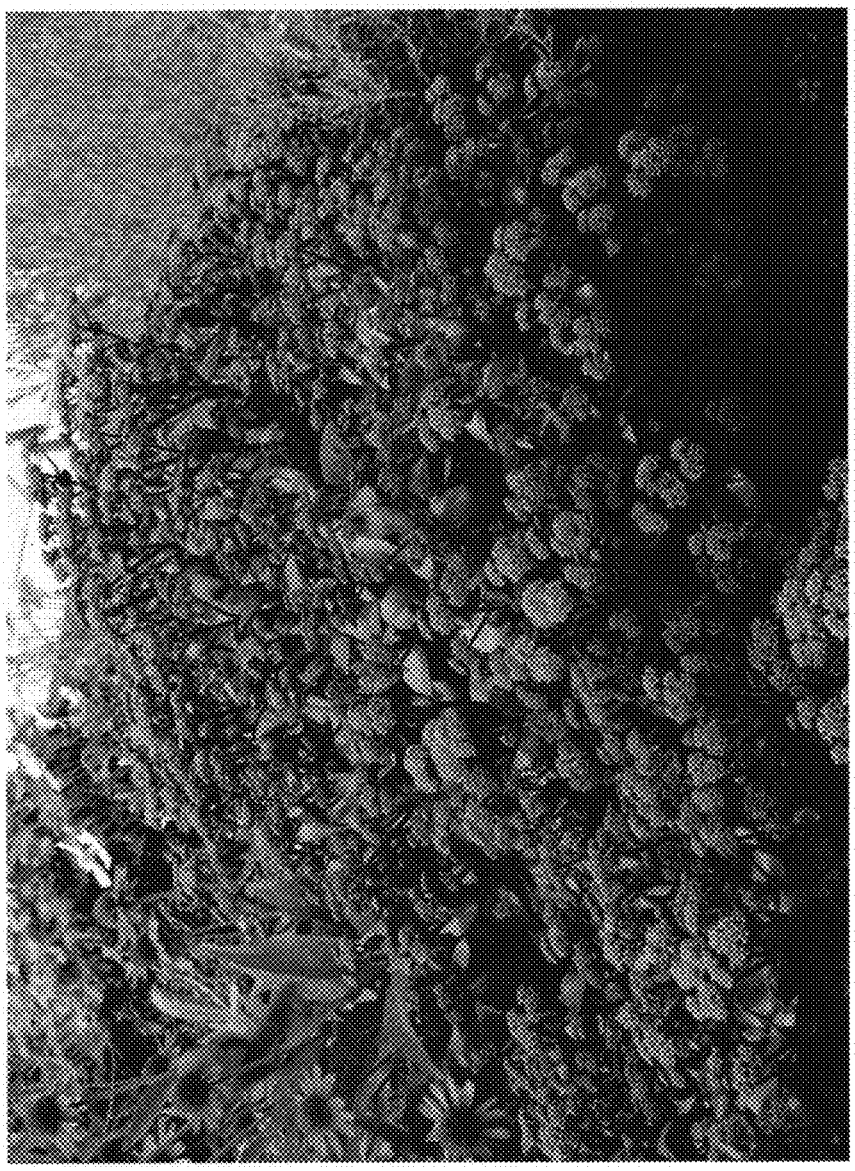

* * * * *